United States Patent [19]

Wright

[11] 4,223,134
[45] Sep. 16, 1980

[54] PROCESS FOR PREPARING CEPHALOSPORIN ANTIBIOTICS

[75] Inventor: Ian G. Wright, Greenwood, Ind.

[73] Assignee: Eli Lilly and Company, Indianapolis, Ind.

[21] Appl. No.: 964,402

[22] Filed: Nov. 28, 1978

Related U.S. Application Data

[62] Division of Ser. No. 670,487, Mar. 25, 1976, Pat. No. 4,148,817.

[51] Int. Cl.$^2$ .......................................... C07D 501/04
[52] U.S. Cl. ..................................................... 544/26
[58] Field of Search ........................... 424/246; 544/26

[56] References Cited

U.S. PATENT DOCUMENTS

| | | | |
|---|---|---|---|
| 3,694,437 | 9/1972 | Jackson | 424/246 |
| 4,035,361 | 7/1977 | Wheeler | 544/26 |
| 4,064,122 | 12/1977 | Ishimaru | 424/246 |
| 4,098,796 | 7/1978 | Guddal | 544/26 |
| 4,112,088 | 9/1978 | Berges | 544/26 |

Primary Examiner—Paul M. Coughlan, Jr.
Attorney, Agent, or Firm—William B. Scanlon; Arthur R. Whale

[57] ABSTRACT

The silylated and enamine protected D-3- or 4-hydroxyphenylglycine as the sodium salt of the formula

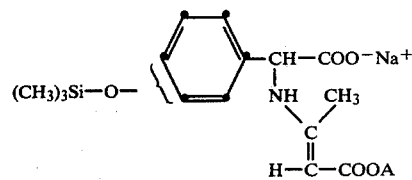

wherein A is methyl or ethyl, are crystalline intermediates useful in a new process for the acylation of heterocyclicthiomethyl-substituted cephalosporin nuclei, e.g. 7-amino-3-(5-methyl-1,3,4-thiadiazole-2-ylthiomethyl)-3-cephem-4-carboxylic acid and 7-amino-3-(1-methyl-1H-tetrazole-5-ylthiomethyl)-3-cephem-4-carboxylic acid.

3 Claims, No Drawings

PROCESS FOR PREPARING CEPHALOSPORIN ANTIBIOTICS

This is a division of application Ser. No. 670,487 filed Mar. 25, 1976, now U.S. Pat. No. 4,148,817.

BACKGROUND OF THE INVENTION

This invention relates to chemical intermediates useful in the preparation of cephalosporin antibiotic compounds. It further relates to a process for the preparation of certain cephalosporin antibiotics. In particular, this invention relates to sodium 3- or 4-(trimethylsilyloxy)phenylglycinate as the enamine formed with methyl or ethyl acetoacetate and to a process for the preparation of 3-heterocyclic-thiomethyl-substituted cephalosporins such as 7-(3- or 4-hydroxyphenylglycylamido)-3-(1-methyl-1H-tetrazole-5-thiomethyl)-3-cephem-4-carboxylic acid and 7-(3- or 4-hydroxyphenylglycylamido)-3-(5-methyl-1,3,4-thiadiazole-2-ylthiomethyl)-3-cephem-4-carboxylic acid. The compounds prepared by the process of this invention have been previously described, for example, by Ryan in U.S. Pat. No. 3,641,021, by Dunn, et al., in U.S. Pat. Nos. 3,867,380 and 3,855,213 and by Cooper in co-pending application Ser. No. 498,886.

The trimethylsilyloxy-enamine-protected hydroxy substituted phenylglycines described herein are useful intermediates in the process of this invention.

SUMMARY OF THE INVENTION

The sodium salt of the enamine formed with 3- or 4-hydroxyphenylglycine and methyl acetoacetate or ethyl acetoacetate is reacted under substantially anhydrous conditions with a trimethylsilylating agent such as hexamethyldisilazane or trimethylsilylacetamide (MSA) to form the trimethylsilyl ether of the hydroxyphenylglycine enamine sodium salt. The trimethylsilyl ether-enamine-salt is isolated as a crystalline white solid and can be stored in a dry atmosphere for future use in the preparation of cephalosporin antibiotics. The trimethylsilyl ether-enamine-salt is converted to the mixed anhydride active derivative formed with methyl or ethyl chloroformate and used in a novel process to acylate a soluble silylated derivative of a 3-heterocyclic-thiomethyl-substituted 7-amino cephalosporin such as 7-amino-3-(5-methyl-1,3,4-thiadiazole-2-ylthiomethyl)-3-cephem-4-carboxylic acid or 7-amino-(1-methyl-1H-tetrazole-5-ylthiomethyl)-3-cephem-4-carboxylic acid. The acylation product is treated in situ with a methanolic solution of the sodium salt of a carboxylic acid to effect the decomposition of both the trimethylsilyl ether group of the phenylglycine side chain and the trimethylsilyl ester group of the silylated nucleus, and to convert the acylation product to the sodium salt form. The sodium salt of the enamine protected product is isolated and is treated with a mineral acid to effect the hydrolysis of the enamine group and provide the cephalosporin antibiotic compound, for example, 7-[D-2-amino-2-(4-hydroxyphenyl)acetamido]-3-(5-methyl-1,3,4-thiadiazole-2-ylthiomethyl)-3-cephem-4-carboxylic acid or 7-[D-2-amino-2-(4-hydroxyphenyl)acetamido]-3-(1-methyl-1H-tetrazole-5-ylthiomethyl)-3-cephem-4-carboxylic acid.

DETAILED DESCRIPTION

This invention provides amino-protected and hydroxy-protected 3- or 4-hydroxyphenylglycine compounds represented by the following formula I,

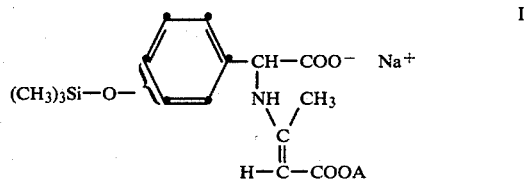

wherein A is methyl or ethyl.

The intermediates represented by the above formula are derivatives of 3- or 4-hydroxyphenylglycine in the sodium salt form wherein the amino group is protected as the enamine formed with methyl or ethyl acetoacetate and the phenolic hydroxyl group is protected with a trimethylsilyl group. These doubly protected hydroxylated phenylglycine intermediates are useful in the preparation of cephalosporin antibiotics wherein the 7-position side chain is an hydroxylated phenylglycyl group.

These cephalosporin antibiotics have been synthesized by acylating the appropriate 7-amino nucleus compound with an amino-protected hydroxyphenylglycine. Following the acylation, the amino protecting group is removed to provide the antibiotic compound. The intermediates represented by formula I wherein both the phenolic hydroxyl group and the α-amino group of the hydrolylated phenylglycine are protected by readily removed protecting groups are uniquely suited in the preparation of these antibiotic compounds. The further protection of the phenolic hydroxyl group via the trimethylsilyl group affords yield advantages as well as improved purity of the antibiotic products when these intermediates are used in the acylation of the appropriate 7-amino nucleus compound.

The compounds represented by formula I can be formally named as derivatives of crotonic acid, for example, 3-[[α-carboxy-3- or 4-[(trimethylsilyl)oxy]benzyl]amino]]crotonic acid, methyl ester, sodium salt. For convenience in the description of this invention, the compounds of formula I will be referred to as the trimethylsilyl ether of 3- or 4-hydroxyphenylglycine enamine sodium salt. As used herein the term "enamine" refers to the enamine formed with methyl acetoacetate or ethyl acetoacetate.

The compounds of formula I are prepared by first converting the hydroxyphenylglycine to the sodium salt, reacting the sodium salt with methyl or ethyl acetoacetate and recovering the crystalline enamine salt. The salt is dried and is then reacted under anhydrous conditions with a trimethylsilylating agent to form the crystalline trimethylsilyl ether of the enamine salt.

The sodium salt of the hydroxyphenylglycine is preferably prepared in methanol as follows. A suspension of the hydroxyphenylglycine in methanol is treated with sodium hydroxide pellets and the mixture heated at a temperature of about 60° C. for about 15 minutes. The sodium salt of the acid forms a thick slurry in methanol.

The salt is then converted to the enamine as follows. Methyl or ethyl acetoacetate is added to the slurry and the mixture heated at the reflux temperature for about 1 to 2 hours. A clear solution of the enamine sodium salt forms. With continued reflux, acetonitrile is added to the solution and the methanol is allowed to distill off. The reaction mixture is allowed to cool to room temperature with stirring and the product enamine salt which crystallizes is collected and dried. The dried enamine salt is then added portionwise to a solution of the trimethylsilylating agent in acetonitrile maintained in a dry atmosphere, for example, dry nitrogen. The mixture is warmed to a temperature of about 50° C. with stirring. Additional acetonitrile is periodically added to the thick slurry to maintain the mixture at a stirrable consistency. The reaction mixture is then cooled to a temperature of about 20° C. and the product is filtered in an atmosphere of dry nitrogen.

Silylating agents which can be employed in the preparation of the compounds of formula I include, for example, monotrimethylsilylacetamide, hexamethyldisilazane, N-trimethylsilyl succinimide, trimethylsilyl methylamine, and like silylating reagents. Bis-trimethylsilyl acetamide can also be employed; however, it imparts orange coloration to the reaction mixture making the purification of the trimethylsilyl ether enamine salt difficult. From an economic standpoint the preferred silylating agent is hexamethylsidilazane.

The trimethylsilyl ethers of the 3- or 4-hydroxyphenylglycine enamine sodium salts are crystalline white compounds which are stable when stored away from contact with moisture.

According to a further aspect of this invention, the trimethylsilyl ethers of formula I are used in an improved acylation process for the preparation of cephalosporin antibiotic compounds represented by the following formula II

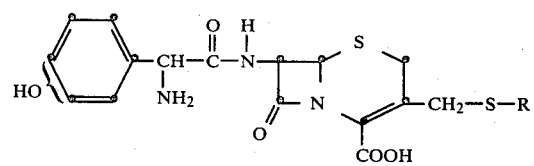

wherein R represents a 5-membered heterocyclic ring substituent selected from the group consisting of

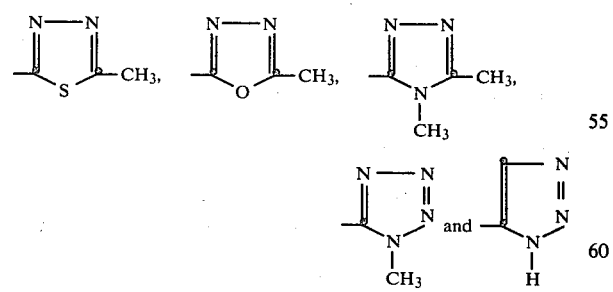

According to the process of this invention, the trimethylsilyl ether of the 3- or 4-hydroxyphenylglycine enamine sodium salt is converted to the active acylating agent by reaction with methyl or ethyl chloroformate to form the mixed anhydride represented by the formula

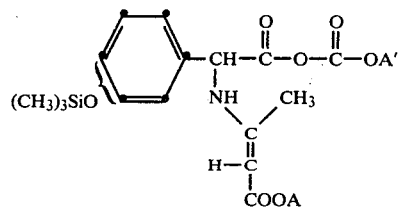

wherein A and A' are methyl or ethyl.

The trimethylsilylated enamine mixed anhydride is then used in the first step of the process in the acylation of a silylated 7-amino-3-heterocyclic-thiomethyl substituted cephalosporin nucleus compound represented by the formula

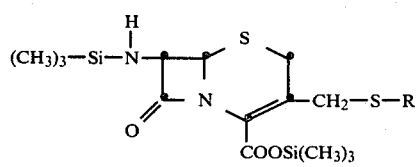

wherein R has the same meanings as defined above.

The acylation product is represented by the following formula

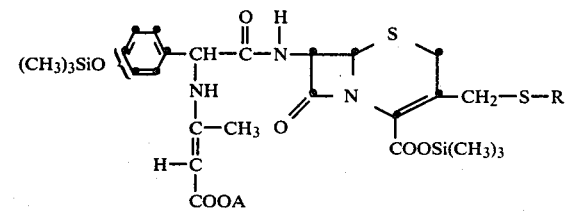

The intermediate trimethylsilyl ether enamine-protected acylation product as the trimethylsilyl ester represented by the above formula is converted in situ to the sodium salt by adding to the reaction mixture a solution of a sodium salt of a carboxylic acid in methanol. The treatment also affects the decomposition of the trimethylsilyl ether group and the trimethylsilyl ester group while the enamine protecting group remains intact. The de-silylated enamine-protected acylation product as the sodium salt represented by the following formula

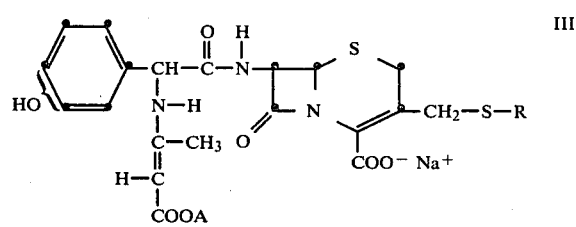

is readily isolated as a stable crystalline solid under the conditions employed in the process of this invention.

The enamine salt of the above formula is then hydrolyzed with a mineral acid in an aqueous medium to effect the removal of the enamine protecting group and provide the antibiotic compound.

Illustrative 7-amino-3-heterocyclic-thiomethyl substituted nucleus compounds used in the process of this invention are 7-amino-3-(1-methyl-1H-tetrazole-5-ylthiomethyl)-3-cephem-4-carboxylic acid, 7-amino-3-(5-methyl-1,3,4-oxadiazole-2-ylthiomethyl)-3-cephem-4-carboxylic acid, 7-amino-3-(1,2,3-triazole-5-ylthiomethyl)-3-cephem-4-carboxylic acid, and 7-amino-3-(1,5-dimethyl-1,3,4-triazole-2-ylthiomethyl)-3-cephem-4-carboxylic acid.

As noted above, the trimethylsilyl ether of the 3- or 4-hydroxyphenylglycine enamine sodium salt represented by formula I is converted to the mixed anhydride formed with methyl or ethyl chloroformate for use as the active acylating agent. The mixed anhydride is prepared as follows. The trimethylsilyl ether enamine sodium salt is added with stirring to a solution of trimethylsilyl succinimide in acetonitrile and the thick slurry is cooled to a temperature of about −35° C. by means of an acetone/dry ice bath. A small amount of dimethylbenzylamine is added to the cold slurry and a slight excess of methyl or ethyl chloroformate is slowly added. As the mixed anhydride forms, the slurry thins and sodium chloride precipitates from the solution. The preparation of the mixed anhydride is carried out in a dry atmosphere, for example, under dry nitrogen.

The mixed anhydride of the trimethylsilyl ether enamine sodium salt is then employed without isolation in the acylation process of this invention which is carried out as follows.

Initially, the 3-heterocyclic-thiomethyl substituted 7-amino cephalosporin nucleus is converted to a soluble silylated derivative for acylation. The silylated derivative of the 7-amino nucleus compound is prepared by suspending the nucleus in acetonitrile and adding to the suspension at about room temperature a 3-molar excess of trimethylsilyl acetamide. The mixture is stirred at ambient temperature until solution is complete. The solution is then cooled to a temperature of between about −15° to −20° C. The silylation of the 7-amino nucleus compound is carried out under substantially anhydrous conditions which are conveniently maintained in an atmosphere of dry nitrogen.

According to the process of this invention the silylated 7-amino nucleus compound is acylated with the mixed anhydride of the trimethylsilyl ether enamine at a temperature between about −50° and 0° C. and preferably at about −25° to about −5° C. The acylation is carried out by slowly adding the cold solution of the silylated 7-amino nucleus compound in a dry nitrogen atmosphere to the solution of the mixed anhydride of the silyl ether of the 3- or 4-hydroxyphenylglycine enamine prepared as described above. The acylation mixture is stirred and is allowed to warm to a temperature of about −5° C. over a 1 to 2 hour period. The reaction temperature is then maintained at about −5° C. until the reaction is complete.

The soluble silylated-enamine-protected acylation product is next converted to the insoluble sodium salt free of silylated functional groups as follows. The acylation reaction mixture is optionally filtered, preferably with a filter aid and the light yellow filtrate is allowed to warm to about 20° C. A solution of a sodium salt of a $C_2$–$C_{10}$ alkyl carboxylic acid in methanol is added to the warmed filtrate with stirring. Meanwhile, a low vacuum is applied to the mixture which is warmed to a temperature of about 30°–35° C. to remove the volatile trimethylsilyl side products formed with methanol. With continued stirring, the enamine protected acylation product (formula III) precipitates from the filtrate as the sodium salt. The mixture is cooled to a temperature of about 20° C., is filtered and the salt washed with acetonitrile and with anhydrous ether. A dry nitrogen atmosphere is maintained over the filtration. The product, which is generally solvated, is dried in vacuo or preferably in a dry nitrogen atmosphere.

Sodium salts of carboxylic acids which can be employed in the process of this invention include the sodium salts of carboxylic acids which are less acidic than the $C_4$ carboxylic acid group of the cephalosporin product. Such salts include, for example, sodium acetate, sodium propionate, sodium butyrate, sodium 2-ethylhexanoate, sodium octanoate and like salts. The preferred sodium salt is sodium 2-ethylhexanoate.

The dried sodium salt of the enamine-protected-acylation product is then hydrolyzed in an aqueous medium under acidic conditions to remove the enamine protecting group to provide the antibiotic compound represented by formula II.

The acidic hydrolysis of the compound of formula III is carried out in aqueous media consisting of water and a water miscible aprotic organic solvent. Solvents such as acetonitrile, tetrahydrofuran, dioxane, dimethylformamide and dimethylacetamide are examples of solvents which can be used with water in the process. A preferred solvent is aqueous acetonitrile.

The acidic hydrolysis is carried out as follows. The dry enamine salt is dissolved in acetonitrile:water (3:1, v:v) at a temperature of about 50° C. Complete solution occurs within a few minutes. Mineral acid is added dropwise to the warm solution until the pH is adjusted to between about 4.0 to about 6.5. The deblocked product begins to precipitate at a pH of about 6.5. The temperature of the solution is maintained at about 50° C. until the pH adjustment and crystallization are complete. The mixture is then cooled to about 10° C. and the product is collected by filtration. The product is washed with a mixture of acetonitrile and water and finally with acetonitrile alone to wash the product free of the colored filtrate. The product can be further decolorized by resuspending the crystalline precipitate in a mixture of acetonitrile:water or other aqueous solvent and refiltering. The crystalline antibiotic can be dried in air or in vacuo to constant weight.

The acid hydrolysis of the enamine sodium salt described above is preferably carried out with nitric acid; however, other mineral acids such as hydrochloric acid and sulfuric acid can be employed. Hydrochloric acid is less preferred since the sodium chloride formed on treatment of the enamine protected cephalosporin salt with the acid causes phase separation of the mixture, thus rendering the isolation of the precipitated product more difficult.

The process of this invention provides excellent yields of high quality crystalline products. The use of the trimethylsilyl protected 3- or 4-hydroxyphenylglycine enamine as described in this process greatly minimizes the formation of side products formed by virtue of the acylation of an unprotected 3- or 4-hydroxy group of the phenylglycine moiety. Under the substantially anhydrous conditions of this process, the trimethylsilyl ether group remains intact until decomposed with methanol following the acylation.

The following hydroxyphenylglycylamido cephalosporin antibiotics are prepared by the process of this invention.

7-[D-2-amino-2-(4-hydroxyphenyl)acetamido]-3-(5-methyl-1,3,4-thiadiazole-2-ylthiomethyl)-3-cephem-4-carboxylic acid, 7-[D-2-amino-2-(3-hydroxyphenyl)acetamido]-3-(5-methyl-1,3,4-thiadiazole-2-ylthiomethyl)-3-cephem-4-carboxylic acid, 7-[D-2-amino-2-(4-hydroxyphenyl)acetamido]-3-(1-methyl-1H-tetrazole-5-ylthiomethyl)-3-cephem-4-carboxylic acid, 7-[D-2-amino-2-(4-hydroxyphenyl)acetamido]-3-(5-methyl-1,3,4-oxadiazole-2-ylthiomethyl)-3-cephem-4-carboxylic acid, 7-[D-2-amino-(4-hydroxyphenyl)acetamido]-3-(1,2,3-triazole-5-ylthiomethyl)-3-cephem-4-carboxylic acid, and 7-[D-2-amino-2-(3-hydroxyphenyl)acetamido]-3-(1-methyl-1H-tetrazole-5-ylthiomethyl)-3-cephem-4-carboxylic acid.

In a preferred embodiment of the process of this invention, the trimethylsilyl ether of the enamine protected 4-hydroxyphenylglycine sodium salt is converted to the mixed anhydride with methyl chloroformate and is used to acylate the trimethylsilylated 7-amino-3-(5-methyl-1,3,4-thiadiazole-2-ylthiomethyl)-3-cephem-4-carboxylic acid. The intermediate silylated-enamine-protected acylation product is treated with a methanolic solution of sodium 2-ethylhexanoate to decompose the silyl protecting groups and to precipitate the enamine protected acylation product as the sodium salt. The sodium salt is then dissolved in a mixture of acetonitrile and water as described above and is acidified with concentrated nitric acid to a pH of about 4.7. The product, 7-[2-amino-2-(4-hydroxyphenyl)acetamido]-3-(5-methyl-1,3,4-thiadiazole-2-ylthiomethyl)-3-cephem-4-carboxylic acid, precipitates from the acidified hydrolysis mixture.

This invention further provides an improved process for the acylation of a 7-amino-3-(heterocyclic-thiomethyl)-3-cephem-4-carboxylic acids of the formula,

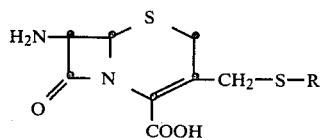

wherein R has the same meanings as defined in formula II, which comprises acylating the nucleus with the mixed anhydride of the compound represented by the formula 1 formed with methyl or ethyl chloroformate. The mixed anhydride of the compound of formula I comprising the trimethylsilyl protecting group and the enamine protecting group permits the acylation to be carried out without competing acylations involving an unprotected phenolic hydroxy group. Acylation with an active derivative of an enamine-protected hydroxyphenylglycine without an hydroxy-protecting group leads to the formation side products formed by the acylation of the free hydroxy group of the acylating agent itself, thus lowering the yield of the desired N-acylated cephalosporin as well as complicating its isolation and purification.

This invention is further illustrated by the following detailed examples.

EXAMPLE 1

To a suspension of 23.9 g. (0.143 M) of D-4-hydroxyphenylglycine in 150 ml. of methanol were added 6 g. (ca. 0.145 M) of sodium hydroxide pellets. The mixture was heated at 60° C. with stirring for about 15 minutes during which time the sodium salt of the acid formed a thick slurry. To the slurry were added 20.1 ml. (0.186 M) of methyl acetoacetate and the mixture was heated at the reflux temperature of approximately 68° C. for 90 minutes. After about 20 minutes at the reflux temperature, a clear solution was obtained and following 20 additional minutes, the product began to crystallize from the clear solution. With continued heating at the reflux temperature, 300 ml. of acetonitrile were added dropwise over a 15 minute period. Thereafter, the solvent methanol was allowed to distill out of the mixture while another 300 ml. of acetonitrile was added dropwise over approximately 75 minutes. The reaction mixture was allowed to cool to room temperature with continued stirring. The crystalline product precipitated at room temperature, was filtered and washed with approximately 200 ml. of acetonitrile. The product, the sodium salt of the methyl acetoacetate enamine of D-4-hydroxyphenylglycine, was dried to yield 40 g. of white, crystalline solid (97 percent yield).

EXAMPLE 2

To a solution of 160 ml. (d=0.774) of hexamethyl disilazane in 250 ml. of acetonitrile in a 3-liter, round bottom, 3-necked flask equipped with a stirrer, thermometer, heating mantle, reflux condenser and a dry nitrogen purge were added 216 g. of finely ground methyl acetoacetate enamine of p-hydroxyphenylglycine sodium salt prepared as described in Example 1. The mixture was warmed to a temperature of about 50°-55° C. with stirring and two drops of trimethylsilyl chloride were added to the thick slurry. Additional acetonitrile totaling 1750 ml. was added periodically to maintain a stirrable consistency. The mixture was kept at 50°-60° C. for about 8 hours and was then cooled to about 20° C. and filtered in an atmosphere of dry nitrogen. The fine white crystalline product was washed with 600 ml. of acetonitrile and 1000 ml. of anhydrous diethyl ether. Trimethylsilylsuccinimide was added to each wash solvent to about a 1 percent concentration to protect the trimethylsilyl group from possible hydrolysis due to any trace amounts of water. The product was dried in an atmosphere of dry nitrogen and stored in a closed container. The weight of dried product was 256 g.

Elemental analysis calculated for $C_{16}H_{22}NO_5SiNa$: Theory: C, 53.46; H, 6.17; N, 3.90; O, 22.26. Found: C, 52.98; H, 6.37; N, 4.07; O, 21.15.

NMR, T60 (DMSO $d_6$)*: δ 0.08, 0.23 (9H, two singlets), 1.67 (3H, s), 3.51 (3H, s), 4.28 (1H, s), 4.75 (1H, d, J=7 Hz), 6.74 (2H, d, J=8 Hz), 7.21 (2H, d, J=8 Hz), and 9.60 (1H, d, J=7 Hz)

*Spectrum calibrated externally with tetramethylsilane. A trace of water in the deuterated dimethylsulfoxide solvent causes partial hydrolysis of the trimethylsilyl group resulting in two signals; the larger signal at 0.23 is the trimethylsilyl ether signal.

EXAMPLE 3

7-[D-2-Amino-2-(4-hydroxyphenyl)acetamido]-3-(5-methyl-1,3,4-thiadiazole-2-ylthiomethyl)-3-cephem-4-carboxylic acid To a dry 5-liter round bottom, 3-necked flask equipped with a stirrer, a cooling bath, a low temperature thermometer, and a dry nitrogen purge are added one liter of dry acetonitrile and 15 g. (87 mM) of trimethylsilyl succinimide. To the solution are added with stirring 256 g. (715 mM) of the trimethylsilyl ether of 4-hydroxyphenylglycine enamine sodium salt prepared as described in Example 2. The thick white slurry which is obtained is cooled to −35° C. by means of an acetone/dry ice bath, 2 ml. of dimethylbenzylamine are added, and 60 ml. of methyl chloroformate (d=1.223, 97 percent) are added in a slow stream over 3 to 5 minutes. The white slurry thins out considerably as the mixed anhydride forms and sodium chloride precipitates from the reaction mixture. The solution of the mixed anhydride is stirred at a temperature of about −35° C. for 20 minutes before a cold solution of the trimethylsilylated 7-amino-3-(5-methyl-1,3,4-thiadiazole-2-ylthiomethyl)-3-cephem-4-carboxylic acid in acetonitrile is added. The solution of the silylated 7-amino-nucleus compound is separately prepared for the acylation as follows.

To a dry 2-liter round bottom, 3-necked flask equipped with a stirrer, a low temperature thermometer, a cooling bath, and a dry nitrogen purge are added 250 ml. of dry acetonitrile, 263 g. (1800 mM) of trimethylsilyl acetamide (90 percent pure), and 215 g. (600 mM) of 7-amino-3-(5-methyl-1,3,4-thiadiazole-2-ylthiomethyl)-3-cephem-4-carboxylic acid (96 percent pure). The mixture is stirred at room temperature until solution is complete, usually within 40 minutes. Just before addition to the mixed anhydride, the solution is cooled to a temperature between about −15° and −20° C. by means of an acetone/dry ice bath.

The cold solution of the silylated 7-amino nucleus compound is then siphoned into the cold solution of the mixed anhydride prepared as described above. The reaction mixture is then allowed to warm to a temperature of about −5° C. over about 2 hours. Approximately 600 ml. of Hyflo filter aid is added to the reaction mixture with stirring and the reaction mixture is filtered through a Hyflo filter pad into a 5-liter round bottom, 3-necked flask, maintained under a dry nitrogen atmosphere. The filter is washed with dry acetonitrile and the light yellow filtrate is warmed to 20° C. with gentle stirring. The solution is seeded with crystalline sodium 7-[D-2-(1-methyl-2-methoxycarbonyl-vinylamino)-2-(4-hydroxyphenyl)acetamido]-3-(5-methyl-1,3,4-thiadiazole-2-ylthiomethyl)-3-cephem-4-carboxylate, the desilylated enamine protected acylation product. A slight vacuum is applied to the seeded solution while 316 ml. of a 1.9 molar solution of sodium 2-ethylhexanoate in dry methanol is added over approximately 5 minutes. The vacuum is maintained to remove the voltatile silyl products and the temperature of the solution is increased to about 30°-35° C. The desilylated enamine protected acylation product as the sodium salt begins crystallizing from the mixture and after approximately 2-3 hours, the temperature of the crystalline mixture is reduced to 20° C. and is filtered. The crystalline product is washed with dry acetonitrile and with anhydrous ether. A dry nitrogen atmosphere is maintained over the filtration. The granular, heavily solvated solid is dried in vacuo to yield 354 g. (96 percent) of the sodium salt of the enamine protected acylation product.

Physical characteristics:
(UV (MeOH) λmax 283 (36,000), 232 (16,500)
$[\alpha]_D^{25\ C.} = +65.2°$ (DMSO)
I.R. (mull) β-lactam 1760 cm$^{-1}$, amide 1664, other carbonyls 1590-1630
N.M.R. (DMSO d6) δ 1.75 (3H, 2), 2.64 (3H, s), 3.31 (1H, d, J=17.5 Hz), ca. 3.4 (1H, broad), 3.51 (3H, s), 3.52 (1H, d, J=17.5 Hz), 4.35 (1H, d, J=12.5 Hz), 4.45 (1H, s), 4.50 (1H, d, J=12.5 Hz), 4.89 (1H, d, J=5 Hz), 5.38 (1H, d, J=8 Hz), 5.53 (1H, d of d., J=5, 8 Hz), 6.74 (2H, d, J=9 Hz), 7.17 (2H, d, J=9 Hz), 9.20 (1H, d, J=8 Hz), 9.26 (1H, d, J=8 Hz).

One liter of a solvent mixture of acetonitrile:water (3:1, v:v) is added to a 2-liter beaker and warmed to a temperature of about 50° C. With stirring, 307 g. of the enamine protected sodium salt prepared as described above are added to the warm solution with stirring. Complete solution occurs in a few minutes. The initial pH of the solution is approximately 7.7. The pH of the solution is adjusted to 4.7 by the dropwise addition of concentrated nitric acid. The solution is maintained at a temperature of 50° C. until crystallization of the product is complete. Thereafter, the mixture is slowly cooled over 1-2 hours to a temperature of about 10° C. The crystalline product, 7-[D-2-amino-2-(4-hydroxyphenyl)acetamido]-3-(5-methyl-1,3,4-thiadiazole-2-ylthiomethyl)-3-cephem-4-carboxylic acid, is collected by filtration and is washed thoroughly with cold solvent (acetonitrile:water 3:1) and also with acetonitrile. The product is dried in air or, alternatively, in vacuo to a constant weight. An 84 percent yield of product, (208 g.) is obtained. When the product is obtained as a very fine crystalline precipitate, the product is best washed by resuspension in fresh solvent mixture and refiltration.

I claim:
1. In the process for preparing a compound of the formula

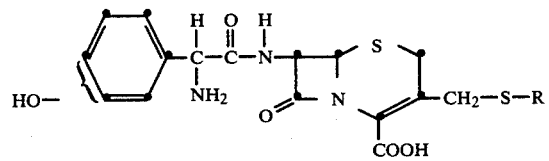

wherein R is

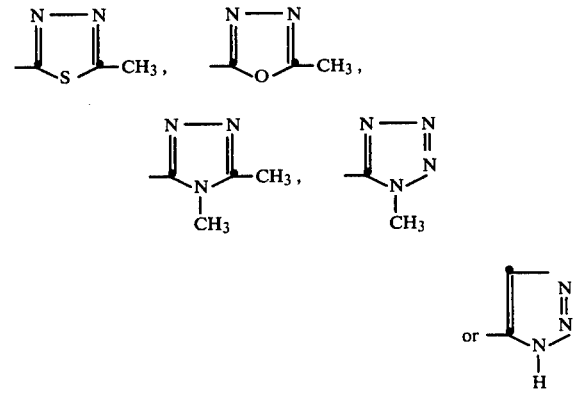

which comprises
(1) acylating a 7-amino nucleus compound of the formula

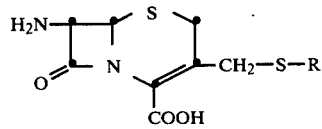

with an amino-protected 3- or 4-hydroxyphenylglycine; and (2) removing the amino-protecting group from the acylation product; the improvement which comprises acylating the 7-amino nucleus compound with the mixed anhydride of a trimethylsilyl ether of an amino-protected phenylglycine compound of the formula

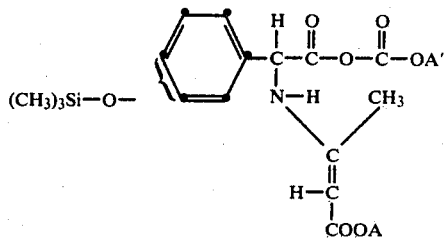

wherein A and A' are methyl or ethyl.

2. The process of claim 1 wherein the enamine-protected phenylglycine silyl ether is a 4-(trimethyl)silyl ether and both A and A' are methyl.

3. The process of claim 1 wherein R is

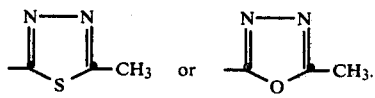

* * * * *